(12) United States Patent
Carlgren et al.

(10) Patent No.: US 7,943,161 B2
(45) Date of Patent: May 17, 2011

(54) CONTRAST AGENT COATED MEDICAL DEVICE

(75) Inventors: Fredrik Carlgren, Lund (SE); Rolf W. Guenther, Aachen (DE)

(73) Assignee: Cook Incorporated, Bloomington, IN (US)

( * ) Notice: Subject to any disclaimer, the term of this patent is extended or adjusted under 35 U.S.C. 154(b) by 0 days.

(21) Appl. No.: 11/297,998

(22) Filed: Dec. 8, 2005

(65) Prior Publication Data
US 2006/0153774 A1  Jul. 13, 2006

Related U.S. Application Data

(60) Provisional application No. 60/634,192, filed on Dec. 8, 2004.

(51) Int. Cl.
*A61B 5/055* (2006.01)
*A61F 2/06* (2006.01)

(52) U.S. Cl. ......... 424/422; 424/9.3; 424/423; 623/1.43

(58) Field of Classification Search ............... 424/9.323, 424/9.4, 423, 426; 600/410, 420, 43, 431–436, 600/458; 514/772.2, 772.3; 623/1.42
See application file for complete search history.

(56) References Cited

U.S. PATENT DOCUMENTS

| 5,300,048 | A |   | 4/1994 | Drewes, Jr. et al. |
| 5,319,059 | A |   | 6/1994 | Neuenschwander et al. |
| 5,824,049 | A | * | 10/1998 | Ragheb et al. ............... 623/1.44 |
| 5,897,536 | A |   | 4/1999 | Nap et al. |
| 6,056,700 | A |   | 5/2000 | Burney et al. |
| 6,585,755 | B2 |  | 7/2003 | Jackson et al. |
| 6,628,982 | B1 | * | 9/2003 | Thomas et al. ............... 600/431 |
| 6,746,481 | B1 | * | 6/2004 | Larik et al. ................... 623/1.45 |
| 2002/0049363 | A1 |   | 4/2002 | Milbocker |
| 2003/0100830 | A1 | * | 5/2003 | Zhong et al. .................. 600/431 |
| 2004/0143180 | A1 |   | 7/2004 | Zhong et al. |
| 2006/0136051 | A1 | * | 6/2006 | Furst et al. ................... 623/1.42 |
| 2007/0014827 | A1 | * | 1/2007 | Larrick et al. ................ 424/423 |

FOREIGN PATENT DOCUMENTS

WO   WO 92/04924   4/1992

* cited by examiner

*Primary Examiner* — Michael G Hartley
*Assistant Examiner* — Jagadishwar R Samala
(74) *Attorney, Agent, or Firm* — Brinks Hofer Gilson & Lione

(57) ABSTRACT

A magnetically opaque medical device is disclosed wherein a contrast agent is incorporated into the actual device. The medical device is generally comprised of a base material forming the structure of the device and a contrast agent, such as tocopherol and tocopherol derivative solutions or suspensions, gadolinium, or nickel sulfate integrated into the base material itself or posited on a substantial portion of an exterior surface of the device. The device may include other additional functional agents and layers.

20 Claims, No Drawings

CONTRAST AGENT COATED MEDICAL DEVICE

RELATED APPLICATIONS

This application is based on and claims priority to provisional patent application No. 60/634,192 filed Dec. 8, 2004.

BACKGROUND

1. Technical Field

The present invention relates generally to medical devices, and more particularly to medical devices that are magnetically opaque and at least partially implantable into a human or veterinary patient. In preferred embodiments, the invention relates to catheters, cannulae and other medical devices with magnetically opaque contrast agents incorporated along a substantial portion of the body of the device.

2. Background Information

It has become common to treat a variety of medical conditions by introducing an implantable medical device partly or completely into the esophagus, trachea, colon, biliary tract, urinary tract, vascular system or other location within a human or veterinary patient. For example, many treatments of the vascular system entail the introduction of a device such as a stent, a catheter, a balloon, a wire guide, a coil, a cannula, or the like. The device utilized may serve a variety of purposes such as maintaining vessel patency, providing access to a body portion, or introducing therapeutic agents. The implantation of these devices, however, can be damaging. Examples of possible damage include disturbance or injury to vessel walls during navigation, occurrences of clot formation, thrombosis, stenosis or occlusion of the vessel and a general risk of infection. Infection has been controlled by incorporating antibiotics into the medical device, for example, by imbedding an antibiotic powder in the device covered by a permeable layer. In such cases, delivery of the antibiotic occurs by way of dispersion from the device, through the permeable layer and into the surrounding tissue.

The medical industry is increasingly using implantable devices on more patients and in new ways. These devices are becoming an important part of surgeries as they limit incisions and intrusion into the body cavity as well as often having a self contained delivery system for therapeutic agents. A wide range of therapeutic agents can be used and include antibiotics, cancer drugs, chemotherapeutic drugs, numerous disease-specific drugs, genetic material, living cells introduced for transplantation and other biological therapeutic agents. Due to their extensive use, the ability to acquire images of the devices while implanted and/or during implantation is essential. Imaging facilitates precisely locating the device as well as visualizing interactions between the biologic tissue and the medical device. Past surgical procedures using implantable devices often incorporated a camera or scope to visualize the area surrounding the medical device, however such practices are intrusive and increase the chances of tearing or otherwise damaging tissue.

While X-ray and other radio imagery techniques are common, magnetic based imaging is becoming more common and preferred. Magnetic Resonance Imaging (MRI) and Magnetoencephalagraphic (MEG) scans are two common magnetic based imaging procedures. MRI is an often used modality for imaging bone, blood vessels and other living tissue through the detection of magnetic resonance of the biologic matter. While MRI can detect the tissue surrounding a removably positioned device, MRI cannot discern the magnetically translucent devices typically used.

The translucency of the medical device makes it difficult to determine its location relative to the organ structures, tissue and cell clusters of interest. Visualization of medical devices while in use is valuable for numerous reasons, including the ability to monitor and evaluate the efficacy of drug delivery in the area of the device, ability to track the devices movements or the ability to accurately determine relative positions of the device when precision is important to the procedure.

Several techniques have been used in attempts to overcome this problem in diagnostic imaging procedures. Generally, magnetically opaque landmarking devices or fiducial markers are used to denote a particular point on or in the body which is visible to MRI. Magnetically opaque fiducial markers are either internal markers inherent in anatomy or external positional markers temporarily affixed to the body, both creating a reference point. External fiducial markers are generally made from or incorporate a magnetically opaque substance, or contrast agent. Contrast agents are various materials that have a discernable magnetic resonance or magnetic moment which can be induced and hence visualized in magnetic imaging. Common contrast agents include arsenic, gadolinium, solutions or suspensions of tocopherol (vitamin E) and its derivatives, metal ions, salts or chelates such as Nickel Sulfate ($NiSO_4$), among others. For example, vitamin E tablets can be placed externally on various points of the body to denote that point during imaging, producing both anatomical and functional information. While markers can often be used as reference points, many areas of the body contain neither an appropriate internal fiducial marker nor an appropriate place to position an external marker containing contrast agents.

In attempts to visualize or track devices, the medical industry has incorporated a magnetically opaque portion into the device or utilized a second instrument used solely as a reference point.

Examples of MRI-visibility enhanced devices include magnetically opaque paramagnetic instrument tips or MRI-visible micro-coil devices attached to the instrument. Such devices only make a discrete portion of the entire device visible and can be bulky and difficult to efficiently incorporate into the medical device. Another device incorporates a contrast agent-containing fluid in a cavity between two concentric lumens of a catheter, the main purpose of which is to allow the variable pressurization of the catheter by the introduction or removal of liquid, as shown in U.S. Pat. No. 5,897,536. The fluid carrying the contrast agent, however, is only introduced when increased stiffness of the device is desired. Furthermore, the disclosed devices are larger in diameter to create a sufficient fluid cavity for pressurization. A medical device according to U.S. Pat. No. 6,056,700 is capable of taking a biopsy of tissue and then leaving a magnetically opaque marker at the site of biopsy, so that the exact position of the biopsy can be precisely found again. That device does not aid MRI guided procedures, but simply leaves an internal marker behind for future reference. Another medical device is rendered partially MRI visible by the application of dysprosium oxide rings, which are magnetically opaque on the catheter or guidewire. The rings are only located at certain increments of the device and may increase diameter of the device.

Completely separate medical devices have been used for the sole purpose of providing a marker or reference point. For example, U.S. Pat. No. 6,628,982 discloses a separate apparatus carrying an MRI detectable material. Separate devices can be inserted into organs or biological substances that are not usually visable for the sole reason of imaging them, as opposed to performing a functional procedure on the surrounding tissue. Separate marking devices can also be used in addition to medical devices such as catheters and stents, however the increased bulk of instruments intruding on the patient increases the chances of trauma, tearing and infection.

It is desirable to manufacture a medical device which incorporates magnetically opaque material throughout a substantial portion of the device. It is desirable that a device not be significantly larger than similar magnetically lucent devices. It is also desirable to minimize the number of devices used during a procedure by placing the contrast agent on or in the functional medical device. It is also desirable to be able to visualize a large portion of a medical device while at least partially implanted, as opposed to a single point or area of the device. It is likewise desirable to use a minimally sized device which is magnetically opaque such that its travel, location and use can be visually tracked by magnetic imaging modalities.

BRIEF SUMMARY

The present invention provides a medical device which incorporates a contrast agent along a portion and/or area of the device. In one embodiment of the invention, a medical device, for at least partial implantation in a patient, comprises a base material and a contrasting agent which can coat or otherwise cover the surface of the base material. In another embodiment of this invention a contrast agent is directly incorporated into the base material defining the device.

In yet another embodiment, the medical device is comprised of a plurality of layers including at least a base material and a contrast agent layer. Additional layers can include any number of combinations of therapeutic agents, coating agents, lubricating agents, antimicrobial agents, biologic agents, porous coatings, non porous coatings or numerous other appropriate agents.

Another embodiment of this invention is a method of making a medical device with a contrast agent incorporated along a substantial portion of the device. In one embodiment, the method comprises forming a base material member defining a medical device and a contrast agent associated with the base material. The integration of the base material and the contrast agent can include commingling of the contrast agent and base material prior to formation of the device or the coating of a surface of the base material with the contrast agent. A coating of contrasting agent can by applied by numerous methods including dipping, spraying, evaporation techniques, plasma deposition, vapor deposition or immersion. Additional steps can include applying additional layers, including therapeutic agents, lubricating agents or other coatings to the device and any subsequent curing of the applied coatings.

There are many ways to practice the present invention, a few of which are shown in the following specification. The embodiments described below are not meant to limit the invention, but rather to describe and illustrate the many ways that the present invention may be used.

DETAILED DESCRIPTION OF THE PRESENTLY PREFERRED EMBODIMENTS

The present invention is directed to a medical device having a magnetically opaque contrast agent which is coating or is otherwise incorporated along a portion of the medical device, allowing imaging of the device in relation to the body or surrounding tissue. The contrast agent can be adhered to a normally magnetically lucent medical device in order to delineate a substantial portion of it during imaging.

Numerous contrast agents are appropriate for this invention and include any compound having a discernable magnetic resonance or magnetic moment. Therefore, during imaging of the general anatomical area in which the device is at least partially implanted, the contrast agent contained in the device can be induced and those portions of the device visualized in magnetic imaging. Suitable contrast agents include gadolinium, solutions or suspensions of tocopherol, tocopherol derivative solutions or suspensions (generally referred to as vitamin E), metal ions, salts or chelates such as Nickel Sulfate ($NiSO_4$), among others. Choice of contrast agent will depend on the method in which it is incorporated, the likelihood of contact between the contrast agent and tissue and the type or purpose of the medical device. For example, vitamin E can function as both an antioxidant as well as a contrast agent. Generally, the contrast agent may be any paramagnetic compound which is visible by MRI and able to differentiate the device from the surrounding tissue. Contrast agents which come into contact with human tissue usually diffuse throughout the body prior to being metabolized or excreted.

The contrast agent is preferably incorporated along a substantial portion of the device. It can be incorporated into the device by several methods ordinarily used, such as those commonly used to incorporate therapeutic agents in medical devices. As will be discussed below, a contrast agent can be applied to at least one surface of the medical device, such as by spraying, dipping, coating, dispersal in the base material of the member, bulk distribution or any desired method. Indeed any technique which incorporates a contrasting agent in or on a medical device which is magnetically visible while in use is appropriate. Because most base materials, therapeutic agents or other coatings are magnetically lucent, the present invention renders the device magnetically opaque so that it can be visualized while in use. For example, a substantial portion of the device can be coated with vitamin E or numerous other contrast agents to allow visualization of any portion of the device so coated.

The invention is suitable for use with any medical device which is at least partially implanted in the patient during an interventional MRI. This invention is also suitable for use with any medical device where magnetic imaging is desirable either during insertion, after insertion or during removal of the device which is either partially or wholly implanted. Magnetic imaging after insertion of the medical device can include those permanently positioned within a patient. Examples of types of devices that can be made in accordance with the present invention include stents, catheters, cannulae, wire guides, balloons and bladders. The stent structure can be used in the vascular system as well as other systems and sites such as the esophagus, trachea, colon, biliary ducts, urethra and ureters, among others. The device can alternatively be any conventional vascular device or other medical device, including a variety of conventional stents and other adjuncts, such as helical wound strands, perforated cylinders, or the like. Moreover, if the device is only partially implanted, only the portion of the device actually positioned within the patient needs to be treated or affected by the contrast agent.

The medical devices according to the present invention can be completely implanted within the body, or only partially implanted within the body. In each scenario, however, at least a portion of the device remains within the subcutaneous space. In a preferred embodiment, the medical device traverses the skin through the epidermis, derma and subcutaneous layers to a vessel. An interface can be formed between the vessel and the lumen of the device, such as by direct insertion of the distal end of the device into the vessel or by attachment of the distal end to the vessel, such as anastomosis. Because the device is implanted transcutaneously, the device in this embodiment includes a portion that remains external to the body. This external portion provides the desired access to the lumen which is in communication with the vessel, thus, the vessel can be accessed without further disruption to the skin.

The medical device comprises a structure adapted for at least partial introduction into a human or veterinary patient and visible to magnetic imaging techniques. Adapted means that the structure is shaped and sized for such introduction. As is common, medical devices according to this invention are preferably comprised of several layered materials. In a preferred embodiment, a base material forms the main structure of the device, to which the desired contrast agent(s) are applied or incorporated. Additional therapeutic, lubricating, or other common coatings can also be applied to the base material. In a preferred embodiment, a contrast agent, such as vitamin E (tocopherol) solution, suspension or a derivative thereof, conventional dilute gadolinium, or Nickel Sulfate ($NiSO_4$), is associated with at least one layer of the device.

The base material of the medical device can be one of numerous conventional materials and need only be acceptable for use in a medical device, i.e., biocompatible and acceptable for the intended use of the device, although occasionally cytotoxic or other poisonous base materials may be employed if they are adequately isolated from the patient. Preferably, the material is able to have at least one contrast agent associated with it. The material chosen will depend on several factors including the intended use of the device, the contrasting and/or therapeutic agents(s) that will be used in the device, the ability of the material to have one or more of the agents associated with it and the permeability of the material.

Examples of suitable base materials include materials for medical devices such as polymers, copolymers, plastics and metals. The base material may be either elastic or inelastic, depending upon the flexibility or elasticity of the polymer layers to be applied over it. The base material may be either biodegradable or non-biodegradable and a variety of biodegradable polymers are known. Moreover, some biologic agents have sufficient strength to serve as the base material. Accordingly, the base material can include at least one of silicone, carbon or carbon fiber, cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, or polytetrafluoroethylene. Alternative base materials can include biocompatible polymeric material or mixtures of copolymers, such as polylactic acid, polyglycolic acid or copolymers thereof, a polyanhydride, polycaprolactone, polyhydroxybutyrate valerate. In addition, base materials can include a biodegradable polymer or mixtures of copolymers, such as proteins, extracellular matrix components, collagen, fibrin or another biologic agent. Lastly, the base material can be a suitable mixture of any of the materials mentioned above.

Silicone is a preferred base material for use in one or all of the implantable portions of the devices according to the present invention. Silicone is preferred for several reason, including its widespread use in a variety of medical devices, its known biocompatibility, its permeability to numerous sizes, shapes and types of agents, and its ability to associate with agents by coating, bulk distribution and combinations of these approaches. Also, silicone is readily available from a variety of commercial sources in various forms, including powder form which can be readily used in bulk distribution methods.

The cross-sectional shape of the medical device can be any shape suitable for the types of procedures in which the device will be utilized. A circular cross-sectional shape is particularly preferable in embodiments in which the device comprises a cannula. A circular cross-sectional shape maximizes space within the lumen of the cannula while also providing a suitable shape for interfacing with a body vessel. Furthermore, the medical device can have any suitable configuration of lumen(s), and the chosen configuration will depend on the application for which the device is used. Single and multilumen configurations can be utilized.

A contrast agent can be applied to or incorporated into the base material of the medical device. This can be done in several ways, by several methods, and in numerous sequences. For example, the contrast agent can be admixed into the chosen base material or it can be applied to the outer surface of the base material, for example by any of spraying, dipping, coating, or bulk distribution, or other common application techniques. Furthermore, one or more additional coatings, such as therapeutic agents, lubricating agents, and porous or nonporous layers, can be applied below, on top of or mixed in with the contrast agent, or the contrast agent could likewise be incorporated into any of the additional layers. Contrast agent incorporation can, but does not have to, restrict or deter the agent's contact with surrounding biological tissue. Depending on how the contrast agent is incorporated, agents such as vitamin E are perfectly safe to expose to tissue and can even be beneficial. A vitamin E coating may further help to act as an antioxidant and to help with immune function. Such dispersion, however, may interfere with imaging since the contrast agent will be present in tissue as well. Based on the desired length of time of use of the device, length of needed imaging and general purpose of the procedure, the contrast agent may be incorporated so that it does not disperse, so that it does disperse, or so that it disperses slowly.

In a preferred embodiment, the contrast agent is posited atop the base material of the structure. The contrast agent may be uniformly sprayed, dip coated or applied in an appropriate solvent to the surface of the device, preferably over the portion to be inserted into the patient. In such a case, it may be highly advantageous to surface process or surface activate the base material to promote the deposition or adhesion of the contrast agent on the base material. Such surface modifications include, but are not limited to, cleaning of the device surface with isopropyl alcohol, TDMAC coating and/or grit blasting with a salt (e.g., sodium bicarbonate or sodium chloride), application of glass beads, aluminum oxide or walnut shells, etching, drilling, cutting, abrasion or chemical modifications such as solvent treatment, the application of primer coatings, the application of surfactants, plasma treatment, ion bombardment and covalent bonding. The process is dependent on the amount of contrast agent that can be applied to the surface without falling off or shearing off easily and the viscosity of the agent being used. Vitamin E, for example, can be utilized in a liquid gel type viscosity as vitamin E acetate or in combination with soybean and coconut oil. It is also available as a softgel in the form of di-alpha tocopheryl acetate between 200 I.U. to over 1000 I.U.

In a preferred embodiment, the layer of contrast agent contains preferably about 0.01 mg to about 10 mg and more preferably from about 0.1 mg to about 4 mg of contrast agent per $cm^2$ of the gross surface area of the structure. In other terms, about 100 ug to about 300 ug of drug per 0.001 inch of coating thickness may be contained on the device surface.

In another preferred embodiment, contrast agents can be injected or otherwise included in wells, grooves or other appropriate channel formations integrated into the shape of the device itself as formed by the base material. In such an embodiment, any pattern, length or width of the wells or grooves is appropriate, as long as the general shape, outline, length or other substantial portion of the device is rendered magnetically opaque. How much or what portions of the device is magnetically visible can differ based on the type of device and its intended purpose.

Alternatively, another preferred embodiment has the contrast agent admixed into the base material. Appropriate contrast agents can be included in appropriate base materials, such that when the base material is formed into the medical device, by hardening, curing, extruding or other practices the contrast agent is inexorably present within the entire body of the device. Such incorporation of the contrast agent would clearly delineate the medical device when imaged by a magnetic modality since the agent is concomitant with the device itself.

In yet another embodiment, the medical device comprises two concentric lumens which form an annular space between them to accommodate a contrast agent. The annular space need only be large enough to accommodate sufficient amounts of contrast agent such that the device will be visible. In such a case, the lumens can be made from either porous or nonporous materials. If desired, a seal can be placed at either ends of the lumen to enclose the formed annular space, to prevent or inhibit diffusion of the contrast agent from that space into the surrounding tissue.

In another preferred embodiment, at least one additional layer or coating is applied to the device, in addition to the base material and contrast agent. The additional layers are often functional and can aid in insertion, use, control and structure of the medical device. Such functional layers can include therapeutic layers, as previously discussed, as well as simple coatings or primers, lubricating agents, porous diffusion controlling layers or enclosing nonporous layers, among others. The additional layer(s) or coating(s) can be applied to the device in numerous ways, as previously mentioned. Typically, the solution can be applied to the device by either spraying the solution onto the device or immersing the device in the solution. Whether one chooses application by immersion or application by spraying depends principally on the viscosity and surface tension of the solution, however, it has been found that spraying in a fine spray such as that available from an airbrush will provide a coating with the greatest uniformity and will provide the greatest control over the amount of coating material to be applied to the device. In a coating applied either by spraying or by immersion, multiple application steps are generally desirable to provide improved coating uniformity and improved control over the amount of contrast agent to be applied to the device. Surface processing can again be used to promote deposition or adhesion of additional coating layers, if present.

The coatings used are commonly UV (ultra-violet)-curable, radiation curable, photo-reactive, photo-immobilizing, or otherwise curable. After preparation of the coating, a suitable solution may be prepared and applied to the desired medical devices. The coating may then be cured by exposing the coating to suitable radiation or photo-energy, such as a UV lamp or other sources of suitable photo-initiating activity.

Other methods of applying layers or coatings to the device are vapor phase deposition and plasma deposition. Preferably, the layer is one that is polymerized from a vapor which is free of any solvent, catalysts or similar polymerization promoters. Also preferably, the polymer in the coating layer is one which automatically polymerizes upon condensation from the vapor phase, without the action of any curative agent or activity such as heating, the application of visible or ultraviolet light, radiation, ultrasound or the like. In yet another technique, a polymer solution may be applied to the device and the solvent allowed to evaporate, thereby leaving a coating of the polymer and any other incorporated agents on the device surface.

In an illustrative embodiment, at least one non-porous layer is posited on the medical device—either before or after the contrast agent has been incorporated or attached to the base material. For example, a nonporous layer may be applied over the contrast agent-infused base material, applied over the base material before contrast agent application or applied over the contrast agent layer to discourage its dissipation into surrounding tissue. A nonporous layer need only be sufficiently impervious to prevent an appreciable interaction between the two layers on either side of the non-porous layer, which could include the base material, surrounding tissue or blood, therapeutic agents or other coatings. A non-porous layer can provide a barrier, if desired, between the contrast agent and biological material such that the contrast agent is unlikely to spread into the tissue, making discernment between the affected tissue and the device difficult.

Non-porous coating materials can include parylene derivatives. In a preferred embodiment of the invention, the non-porous layer can have a thickness in a range from 50 to 500,000 Angtroms (Å), more preferably in a range from 100,000 to 500,000 Å, and illustratively approximately 200,000 Å. In still another aspect of the present invention, the coating layer can be considered an adsorbent layer and/or absorbent layer in which a contrast agent is attached thereto.

In a preferred embodiment, a parylene adhesion promotion coating layer is a thin layer of silane having a thickness in the range of, for example, 0.5 to 5,000 Å and preferably 2 to 50 Å. After appropriate preparation, the medical device is dipped in the silane to apply a very thin layer thereof to the outer surface of the base material. Additional agents can then be attached to the surface of the coating layer, if desired. The continued positing of various agents and coating materials can be done as desired. Numerous agents can be located in or on discrete locations on the exterior of the medical device, or the agents can be blended together and uniformly distributed within or on the surface of the medical device.

The use of nonporous coating layers can permit the use of a toxic or poisonous base material, as mentioned above. Even if the base material of the structure is biocompatible, however, it may be advantageous to isolate it from the blood by use of a substantially nonporous coating layer, including coating the surface of a lumen defined by the base material.

The present invention, therefore, can include medical devices incorporating both contrast agents and at least one other functional coating, such as a therapeutic or lubricating agent. The particular structure of the device as disclosed may be adapted to specific uses in a variety of ways. For example, the device may include additional layers of the same or different functional agents—such as a base material having posited on it, in the following order, a contrast agent, a nonporous layer, a therapeutic agent and a porous later. The particular structure of the device as disclosed may be adapted to specific uses in a variety of ways. The number, order and composition of the layering structure of the device is dependent on the function of the layers themselves, such as whether the layer itself is to be dispersed, whether it is meant to prevent other layers from intermingling, whether it is meant to control the rate of diffusion, or whether it is to aid in some other way.

Such layering is also dependent upon the desired use, outcome and needs of the specific procedure. Considerations include the medical device's purpose, degree of implantation, desired minimization of size, and physical area in which it is to be used. Numerous combinations of the above are possible.

Any additional coating layer itself can similarly be processed to promote the deposition or adhesion of the bioactive material layer.

The details of the construction or composition of the various elements of the contrast agent coated medical device not otherwise disclosed are not believed to be critical to the achievement of the advantages of the present invention, so long as the elements posses the magnetic opacity needed to perform as disclosed. The selection of such details of construction is believed to be well within the ability of one of even rudimentary skills in this area, in view of the present disclosure, and are within the spirit of the invention and the scope of the claims. It is therefore intended that the foregoing detailed description be regarded as illustrative rather than limiting, and that it be understood that it is the following claims, including all equivalents, that are intended to define the spirit and scope of this invention.

The invention claimed is:

1. An implantable medical device comprising:
    a base material forming a structure for introduction into a vessel of a patient, the base material comprising silicone or a silicone derivative, the structure having at least one surface,
    at least one contrast agent layer posited atop the base material and over at least one surface of the structure, the contrast agent comprising tocopherol; and;
    a non-porous poly(p-xylylene)polymer layer posited over the contrast agent layer, wherein the non-porous layer discourage the contrast agent being dissipation into surrounding tissue.

2. The implantable medical device of claim 1, wherein the contrast agent is tocopherol, wherein the contrast agent layer comprises about 0.01 mg to about 10 mg of the contrast agent per $cm^2$ of the gross surface area of the structure, wherein the medical device further comprises a therapeutic agent coating layer posited on the non-porous layer, the therapeutic agent coating layer comprising about 100 μg to about 300 μg of a therapeutic agent per 0.001 inch of the total coating thickness on the device surface.

3. The implantable medical device of claim 1, wherein the contrast agent is applied to the structure by one of dipping, spraying, bulk distribution, plasma deposition or vapor phase deposition.

4. An implantable medical device comprising:
    a base material forming a structure for implantation into a patient, a magnetically opaque contrast agent intermingled in the base material, and a non-porous poly(p-xylylene)polymer coating layer posited over a surface of the base material, wherein the base material comprises silicone or a silicone derivative and forms the main structure of the device, wherein the non-porous layer discourage the contrast agent being dissipation into surrounding tissue.

5. The implantable medical device of claim 1, wherein the contrast agent is tocopherol.

6. The implantable medical device of claim 1, wherein the contrast agent is attached to the surface of an adhesion promotion coating layer formed on an outer surface of the base material.

7. The implantable medical device of claim 6, wherein the coating layer has a thickness between 2 to 50 Å.

8. The implantable medical device of claim 1, wherein the contrast agent is injected or otherwise included in wells, grooves or channel formations integrated into the shape of the device as formed by the base material.

9. The implantable medical device of claim 1, wherein the device comprises a stent, catheter, cannulae, wire guide, balloon or bladder.

10. The implantable medical device of claim 1, wherein the device is configured for vascular system implantation.

11. The implantable medical device of claim 1, wherein the device is a stent.

12. The implantable medical device of claim 4, wherein upon implantation in a patient the non-porous layer is configured to directly face tissue or blood.

13. The implantable medical device of claim 4, wherein the device comprises a stent, catheter, cannulae, wire guide, balloon or bladder.

14. An implantable medical device comprising:
    a base material defining said device for introduction into a patient, the base material comprising silicone or a silicone derivative, the device having at least one surface;
    a contrast agent directly deposited on a surface of the base material; and
    a non-porous layer poly(p-xylylene)polymer deposited over the contrast agent,
    wherein the contrast agent is tocopherol, wherein the non-porous layer discourage the contrast agent being dissipation into surrounding tissue.

15. The implantable medical device of claim 14, wherein upon implantation in a patient the non-porous layer is configured to directly face tissue or blood.

16. The implantable medical device of claim 14, wherein a therapeutic agent layer is deposited over the non-porous layer and a porous layer is deposited over the therapeutic layer.

17. An implantable medical device comprising:
    a base material forming a structure for implantation into a patient, a contrast agent directly incorporated into the base material, and a non-porous poly(p-xylylene)polymer coating layer posited over a surface of the base material, wherein the base material comprises silicone and forms the main structure of the device, and wherein the non-porous layer prevents the contrast agent layer from being in contact with the vessel of the patient.

18. The implantable medical device of claim 17, wherein tocopherol is directly incorporated into the base material.

19. The implantable medical device of claim 17, wherein a tocopherol solution or tocopherol suspension is directly incorporated into the base material.

20. The implantable device of claim 1, wherein the contrast agent layer has a first surface portion in contact with the base material and a remaining portion in contact with the non-porous layer.

* * * * *